(12) United States Patent
Pinchasik

(10) Patent No.: US 7,763,064 B2
(45) Date of Patent: Jul. 27, 2010

(54) STENT HAVING STRUTS WITH REVERSE DIRECTION CURVATURE

(75) Inventor: Gregory Pinchasik, Herzeliya (IL)

(73) Assignee: Medinol, Ltd., Tel Aviv (IL)

( * ) Notice: Subject to any disclaimer, the term of this patent is extended or adjusted under 35 U.S.C. 154(b) by 372 days.

(21) Appl. No.: 10/864,685

(22) Filed: Jun. 8, 2004

(65) Prior Publication Data

US 2005/0273157 A1    Dec. 8, 2005

(51) Int. Cl.
*A61F 2/86* (2006.01)
(52) U.S. Cl. ...................................... 623/1.15
(58) Field of Classification Search ............... 623/1.15, 623/1.16, 1.2
See application file for complete search history.

(56) References Cited

U.S. PATENT DOCUMENTS

| | | | | |
|---|---|---|---|---|
| 4,733,665 A | 3/1988 | Palmaz | ....................... | 128/343 |
| 4,755,593 A | 7/1988 | Lauren | ....................... | 530/356 |
| 4,886,062 A | 12/1989 | Wiktor | ....................... | 128/343 |
| 5,037,377 A | 8/1991 | Alonso | ....................... | 600/36 |
| 5,102,417 A | 4/1992 | Palmaz | | |
| 5,104,404 A | 4/1992 | Wolff | | |
| 5,133,732 A | 7/1992 | Wiktor | ....................... | 606/195 |
| 5,510,077 A | 4/1996 | Dinh et al. | ................... | 264/485 |
| 5,554,181 A | 9/1996 | Das | | |
| 5,554,182 A | 9/1996 | Dinh et al. | ....................... | 623/1 |
| 5,571,166 A | 11/1996 | Dinh et al. | ....................... | 623/1 |
| 5,575,818 A | 11/1996 | Pinchuk | ........................ | 623/1 |
| 5,591,224 A | 1/1997 | Schwartz et al. | ................ | 623/1 |
| 5,595,571 A | 1/1997 | Jaffe et al. | .................... | 8/94.11 |
| 5,603,721 A | 2/1997 | Lau et al. | | |
| 5,628,785 A | 5/1997 | Schwartz et al. | ................ | 623/1 |
| 5,632,771 A | 5/1997 | Boatman et al. | | |
| 5,653,747 A | 8/1997 | Dereume | ....................... | 623/1 |

(Continued)

FOREIGN PATENT DOCUMENTS

DE    19512066    11/1996

(Continued)

OTHER PUBLICATIONS

Singapore Examination Report.

(Continued)

*Primary Examiner*—Anhtuan T Nguyen
*Assistant Examiner*—Ryan J Severson
(74) *Attorney, Agent, or Firm*—Cadwalader Wickersham & Taft LLP

(57) ABSTRACT

Disclosed is a stent having struts with reverse direction curvature for providing a reduced compressed profile and an increased expanded profile. The strut configuration comprises a plurality of arcuate sections facing in opposite convex and a concave orientation. The strut width may be gradually decreased from its ends towards the strut's mid-section to redistribute maximal strains away from portions of the stent more susceptible to permanent deformation, such as the loop portions. Varying strut lengths to offset the maximum circumferential widths of adjacent portions of the stent may further reduce the compressed stent profile. The varied stent lengths may also contribute to an increased expanded stent profile. Stents with the reverse direction curvature strut design can obtain an expanded to compressed stent diameter ratio of about 7:1 compared to conventional stents that have a ratio of up to about 5:1. The curved strut can be utilized with any stent design.

22 Claims, 13 Drawing Sheets

U.S. PATENT DOCUMENTS

| | | | |
|---|---|---|---|
| 5,693,085 A | 12/1997 | Buirge et al. | 623/1 |
| 5,720,777 A | 2/1998 | Jaffe et al. | 623/2 |
| 5,733,303 A | 3/1998 | Israel et al. | |
| 5,800,507 A | 9/1998 | Schwartz | 623/1 |
| 5,800,508 A | 9/1998 | Goicoechea et al. | 623/1 |
| 5,807,404 A | 9/1998 | Richter | 623/1 |
| 5,836,964 A | 11/1998 | Richter et al. | 606/194 |
| 5,843,180 A | 12/1998 | Jaffe et al. | 623/2 |
| 5,843,181 A | 12/1998 | Jaffe et al. | 623/1 |
| 5,849,034 A | 12/1998 | Schwartz | 623/1 |
| 5,855,597 A | 1/1999 | Jayaraman | 623/1 |
| 5,855,600 A | 1/1999 | Alt | 623/1 |
| 5,865,723 A | 2/1999 | Love | 600/36 |
| 5,879,381 A | 3/1999 | Moriuchi et al. | |
| 5,895,407 A | 4/1999 | Jayaraman | 606/198 |
| 5,913,895 A | 6/1999 | Burpee et al. | |
| 5,922,020 A | 7/1999 | Klein et al. | |
| 5,922,021 A | 7/1999 | Jang | 623/1 |
| 5,925,061 A | 7/1999 | Ogi et al. | |
| 5,931,867 A | 8/1999 | Haindl | |
| 5,997,973 A | 12/1999 | Bianca, Jr. | 428/57 |
| 6,013,091 A | 1/2000 | Ley et al. | 606/191 |
| 6,017,365 A | 1/2000 | Von Oepen | 623/1 |
| 6,027,527 A | 2/2000 | Asano et al. | |
| 6,042,606 A * | 3/2000 | Frantzen | 623/1.18 |
| 6,053,941 A | 4/2000 | Lindberg et al. | 623/1 |
| 6,120,847 A | 9/2000 | Yang et al. | 427/335 |
| 6,132,461 A | 10/2000 | Thompson | 623/1.15 |
| 6,159,237 A | 12/2000 | Alt et al. | 623/1.11 |
| 6,179,868 B1 | 1/2001 | Burpee et al. | 623/1.17 |
| 6,183,353 B1 | 2/2001 | Frantzen | 451/104 |
| 6,190,403 B1 | 2/2001 | Fischell et al. | |
| 6,190,406 B1 | 2/2001 | Duerig et al. | |
| 6,193,747 B1 | 2/2001 | Von Oepen | 623/1.15 |
| 6,197,048 B1 | 3/2001 | Richter | |
| 6,221,098 B1 | 4/2001 | Wilson et al. | 623/1.11 |
| 6,224,625 B1 | 5/2001 | Jayaraman | |
| 6,231,598 B1 | 5/2001 | Berry et al. | 623/1.15 |
| 6,240,615 B1 | 6/2001 | Kimes et al. | |
| 6,241,762 B1 | 6/2001 | Shanley | 623/1.17 |
| 6,251,134 B1 | 6/2001 | Alt et al. | 623/1.16 |
| 6,264,689 B1 | 7/2001 | Colgan et al. | |
| 6,273,910 B1 | 8/2001 | Limon | |
| 6,299,604 B1 | 10/2001 | Ragheb et al. | 604/265 |
| 6,312,459 B1 | 11/2001 | Huang et al. | |
| 6,325,825 B1 * | 12/2001 | Kula et al. | 623/1.3 |
| 6,348,065 B1 | 2/2002 | Brown et al. | 623/1.16 |
| 6,383,213 B2 | 5/2002 | Wilson et al. | 623/1.11 |
| 6,387,120 B2 | 5/2002 | Wilson et al. | 623/1.11 |
| 6,409,753 B1 * | 6/2002 | Brown et al. | 623/1.15 |
| 6,416,538 B1 | 7/2002 | Ley et al. | 623/1.15 |
| 6,428,569 B1 | 8/2002 | Brown | 623/1.15 |
| 6,440,162 B1 | 8/2002 | Cox et al. | |
| 6,464,719 B2 | 10/2002 | Jayaraman | |
| 6,471,980 B2 | 10/2002 | Sirhan et al. | |
| 6,478,815 B1 | 11/2002 | Alt | 623/1.115 |
| 6,485,508 B1 | 11/2002 | McGuinness | |
| 6,511,505 B2 | 1/2003 | Cox et al. | |
| 6,540,774 B1 | 4/2003 | Cox | |
| 6,540,775 B1 | 4/2003 | Fischell et al. | |
| 6,562,065 B1 | 5/2003 | Shanley | |
| 6,569,180 B1 | 5/2003 | Sirhan et al. | |
| 6,579,310 B1 | 6/2003 | Cox et al. | |
| 6,602,226 B1 | 8/2003 | Smith et al. | |
| 6,602,281 B1 | 8/2003 | Klein | |
| 6,602,282 B1 | 8/2003 | Yan | |
| 6,605,107 B1 | 8/2003 | Klein | |
| 6,607,554 B2 | 8/2003 | Dang et al. | |
| 6,645,240 B2 | 11/2003 | Yee | |
| 6,648,911 B1 | 11/2003 | Sirhan et al. | |
| 6,656,220 B1 | 12/2003 | Gomez et al. | |
| 6,673,106 B2 | 1/2004 | Mitelberg et al. | |
| 6,699,278 B2 | 3/2004 | Fischell et al. | |
| 6,706,061 B1 | 3/2004 | Fischell et al. | |
| 6,709,453 B2 | 3/2004 | Pinchasik et al. | |
| 6,723,119 B2 | 4/2004 | Pinchasik et al. | |
| 6,821,292 B2 * | 11/2004 | Pazienza et al. | 623/1.15 |
| 7,037,330 B1 | 5/2006 | Rivelli, Jr. et al. | |
| 2001/0053930 A1 | 12/2001 | Kugler et al. | |
| 2001/0056298 A1 | 12/2001 | Brown et al. | 623/1.16 |
| 2002/0004677 A1 | 1/2002 | Jayaraman | |
| 2002/0007212 A1 | 1/2002 | Brown et al. | 623/1.16 |
| 2002/0049490 A1 | 4/2002 | Pollock | |
| 2002/0055770 A1 | 5/2002 | Doran et al. | 623/1.15 |
| 2002/0103529 A1 | 8/2002 | Pinchasik et al. | 623/1.15 |
| 2002/0116049 A1 | 8/2002 | Girton et al. | 623/1.15 |
| 2002/0123798 A1 | 9/2002 | Burgermeister | |
| 2002/0138136 A1 | 9/2002 | Chandresekaran et al. | 623/1.34 |
| 2002/0177893 A1 | 11/2002 | Brown et al. | 623/1.16 |
| 2002/0198593 A1 * | 12/2002 | Gomez et al. | 623/1.16 |
| 2004/0039439 A1 | 2/2004 | Gomez et al. | |
| 2004/0088043 A1 | 5/2004 | Klein | |
| 2004/0204751 A1 | 10/2004 | Fischell et al. | |
| 2005/0043782 A1 | 2/2005 | Gomez et al. | |

FOREIGN PATENT DOCUMENTS

| | | |
|---|---|---|
| DE | 297 08 879 U1 | 9/1997 |
| DE | 197 53 123 A1 | 8/1999 |
| DE | 199 00 411 A1 | 7/2000 |
| DE | 19957063 | 8/2001 |
| EP | 0 623 354 A1 | 11/1994 |
| EP | 0 830 853 A1 | 3/1998 |
| EP | 0 958 794 A2 | 12/1999 |
| EP | 0 958 794 A3 | 12/1999 |
| EP | 0 970 664 A2 | 1/2000 |
| EP | 0876216 | 4/2000 |
| EP | 1 020 166 A1 | 7/2000 |
| EP | 1129673 A2 | 9/2001 |
| FR | 2 758 253 A1 | 7/1998 |
| NZ | 280547 | 9/1998 |
| NZ | 285241 | 3/1999 |
| NZ | 331532 | 1/2000 |
| WO | 95/03010 | 2/1995 |
| WO | WO 96/26689 | 9/1996 |
| WO | WO 97/07889 | 3/1997 |
| WO | 97/32544 | 9/1997 |
| WO | WO 97/32544 | 9/1997 |
| WO | WO 98/35634 | 8/1998 |
| WO | 99/15108 | 4/1999 |
| WO | 99/39660 | 8/1999 |
| WO | WO 99/44543 | 9/1999 |
| WO | 99/62431 | 12/1999 |
| WO | 00/30563 | 6/2000 |
| WO | 00/30563 A | 6/2000 |
| WO | WO 00/30563 | 6/2000 |
| WO | 00/49971 A | 8/2000 |
| WO | WO 02/34163 A2 | 2/2002 |

OTHER PUBLICATIONS

New Zealand Examination Report.
German Office Action.
Cancellation Proceeding against DE Patent No. 20108764.
Cancellation Proceeding against DE Patent No. 20108765.
Two European Search Reports.
PCT Search Reports.
IDS Letter.
European Search Report dated Dec. 2, 2003.
Patent Act 1977: Search Report under Section 17.
European Patent Office, Supplementary European Search Report dated Apr. 11, 2008, for EP 05 75 1740.1.

* cited by examiner

STENT HAVING STRUTS WITH REVERSE DIRECTION CURVATURE

FIELD OF THE INVENTION

The present invention relates generally to a structure for lumenal prostheses. More particularly, the present invention relates to a stent having a reduced compressed profile and an enlarged expanded profile.

BACKGROUND

Lumenal prostheses are used for a variety of medical purposes. Stents, for example, can be placed in various body lumens, such as a blood vessel, biliary tract and gastrointestinal tract, for maintaining patency.

Stents placed in a blood vessel or a coronary artery are typically used to maintain the opening of the vessel wall. In order to do this, the stent must be deployed to the site within the vessel where support is needed, which can be accomplished in a variety of ways. In one common procedure, referred to as percutaneous transluminal coronary angioplasty (PTCA), a balloon catheter is used to open the vessel walls for creating a passageway. A stent is then placed in the newly opened passageway to prop open the vessel. An alternative method of stenting is direct stenting. Direct stenting is a medical technique in which dilatation occurs following implantation of the stent. It is believed that direct stenting may lead to less injury and result in less recurrent in-stent restenosis.

The stent may be self-expanding or balloon-expandable. Self-expanding and balloon-expandable stents are positioned at the deployment site of a vessel via a stent delivery system, which typically includes a delivery catheter. The self-expanding stents are compressed around the outside of the delivery catheter. A retractactable sheath is typically utilized to deploy the self-expanding stent. The stent is then maneuvered through a tortuous path of the patient's vasculature to the deployment site. It is advantageous for the stent to have a small outside diameter or profile in order to be maneuvered through and deployed in a restricted area such as an atherosclerotic site of a blood vessel.

Stents are categorized by a so-called "ratio" that is a measure of the outside diameter of the stent in its expanded state compared to the outside diameter of the stent in its compressed state. Present day stents typically have an expanded to compressed stent diameter ratio up to about 5:1. This relatively small ratio between the expanded and compressed diameters restricts the applications of currently available stents. For example, a stent having a profile small enough to permit the stent to be maneuvered through small diameter vessels would not have a large enough expanded diameter to be deployed in large vessels.

Present day large diameter stents typically have larger strut lengths than small diameter stents. The compressed diameter of current large diameter stents is limited due to interference between adjacent struts. In addition, in self-expandable stents, interference between adjacent struts may subject a portion of a strut to high stress/strain concentrations which may prevent the stent from fully expanding when deployed. For example, if a self-expanding stent is compressed beyond its elastic limit in an attempt to provide a smaller outside diameter, the stent will not return to its desired deployed expanded diameter due to permanent deformation. In addition, large strut lengths decrease the flexibility of the stent, as well as the scaffolding and coverage of the vessel wall when deployed.

Therefore, a need exists for a stent that has a large ratio between expanded and compressed diameters. This increased ratio will allow the stent to be used in more clinical situations than a stent with a smaller ratio. In addition, a need exists for a stent with the capability of minimizing the compressed profile of the stent while achieving optimal strain distribution. In tightly compressed stents, the distribution of strains to more suitable parts of the stent is needed in order to provide a stent capable of expanding to its fully intended diameter. Finally, a need exists for a stent that optimizes strut length to increase the expanded or deployed stent diameter without the detrimental effects of increased strain or compressed profile.

SUMMARY OF THE INVENTION

The present invention provides a stent with an increased expansion to compression ratio compared to currently available stents. Specifically, a self-expandable stent of the present invention have an expansion/compression ratio of about 7:1, whereas conventional self-expandable stents typically have an expansion/compression ratio up to about 5:1. The increased expansion/compression ratio of the stents of the present invention may be achieved by decreasing the compressed diameter of the stent when it is compressed on or in the stent delivery system and/or increasing the expanded diameter of the stent when it is deployed.

Stents of the present invention may be adapted to have a reduced compressed profile compared to conventional stents by utilizing struts with reverse direction curvature. Each strut has opposing arcuate curves or arches extending from each end to about its mid-section. These opposing curves join together at about the midsection of the strut, but are not necessarily limited to joining at this location. Each two adjacent struts in a circumferential section of the stent are joined at an end by a loop. When the stent is compressed, the struts straighten and extend. Due to this configuration, the largest circumferential width of each set of loop and adjoining struts of stent may be significantly reduced thereby reducing the overall compressed diameter of the stent.

Utilizing variable length struts within a circumferential section of the stent may further increase the expansion to compression ratio as shown in the various embodiments of the stent of the present invention. By varying the lengths of the struts in a circumferential section of the stent, the largest circumferential widths of adjacent sets of loops and adjoining struts may be offset. Accordingly, the largest circumferential widths of adjacent sets of loops and adjoining struts will not interfere with each other and impede the compression of the stent. In addition, increasing the lengths of some of the struts will enable the stent to have an increased expanded diameter when deployed.

The expansion to compression ratio may be further increased by a redistribution of the stress/strain forces imparted in the stent, preferably toward the strut sections, during stent compression to prevent permanent deformation of the stent or material failure. When compressed, conventional stents experience high concentrations of stress/strain in the loop sections of the stent. If the levels of stress/strain exceed the elastic limits (reversible strain) of the self-expanding stent, the stent will become permanently deformed and will not fully expand when deployed. The stress/strain imparted on the various embodiments of the present invention may be redistributed by varying the relative strength or flexibility of different portions of the stent. For example, the amount of material used to form different portions of the stent can be varied to change the portions' relative strength or flexibility. This variation can be accomplished by increasing the thickness or width of the loop portions to increase the strength of these portions relative to the strut portions. Preferably, the strut width is also gradually decreased from both ends towards the strut's midsection to further redistribute stress/strain forces away from the loop portions and toward the midsection of the strut portion of the stent.

The reverse direction curvature design of the strut of the present invention also increases the flexibility of the strut relative to that of the loop so that the stent can be further compressed without exceeding its elastic limit. Specifically, the junction in the midsection of the strut between opposing concave and convex curvatures in the strut has increased flexibility relative to the other portions of the strut and the loop. Accordingly, when the stent is compressed the compression forces are redistributed from the loop portions of the stent to the midsection of the strut portions.

These aspects and other objects, features, and advantages of the present invention is described in the following Detailed Description which is to be read in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

The present invention is preferably used with self-expanding stents, but is not limited to applications involving only self-expanding stents. The following detailed description will describe embodiments involving self-expanding stents, however, variations of the invention may be used with balloon-expandable stents and the like.

Self-expanding stents may be delivered to the deployment site using a delivery catheter system balloon catheter. The self-expanding stent is typically placed within a tube located at the distal end of the catheter that places physical limitations on the stent. The tube places physical limitations on the stent and retains the stent in its compressed state until it reaches the deployment site. It is desirable to compress the stent to its smallest possible diameter to minimize the profile of the delivery system. This minimized profile allows the delivery system to navigate the stent through narrow restrictions, where ultimately the stent is deployed at the desired site.

Figure 1:
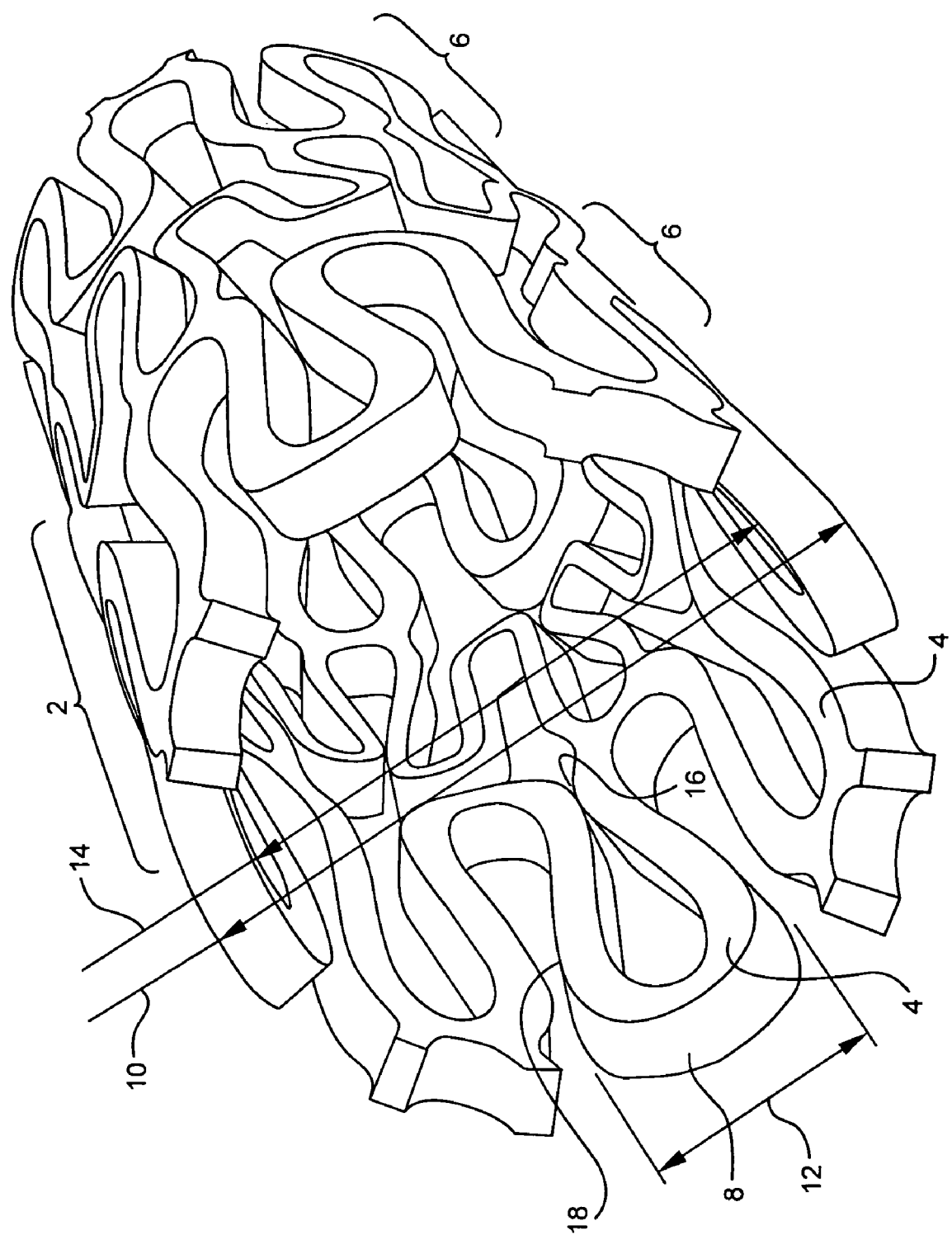
FIG. 1 is a perspective view of a portion of a conventional stent in the compressed state.

FIG. 1 illustrates a conventional stent 2 in the compressed state. Conventional stent 2 includes serpentine sections 6 having struts 4 and loops 8. The stent has an outside diameter 10 and an inside diameter 14.

The largest circumferential width 12 of a loop 8 and the adjoining struts 4 as shown in FIG. 1 determines the extent to which the stent may be compressed as measured by outside diameter 10. In the compressed state, the adjacent sets of loop 8 and adjoining struts 4 may or may not make contact with each other. An example of adjacent sets of loop and adjoining struts in contact with each other is shown at contact site 16. If contact is made, the interference of the adjacent sets of loop 8 and adjoining struts 4 prevent further reduction in the outside diameter 10 of the stent. Accordingly, the extent to which a conventional stent can be compressed is limited by the contact or interference between the bowed regions 18 of adjacent sets of loop 8 and adjoining struts 4.

Figure 2:
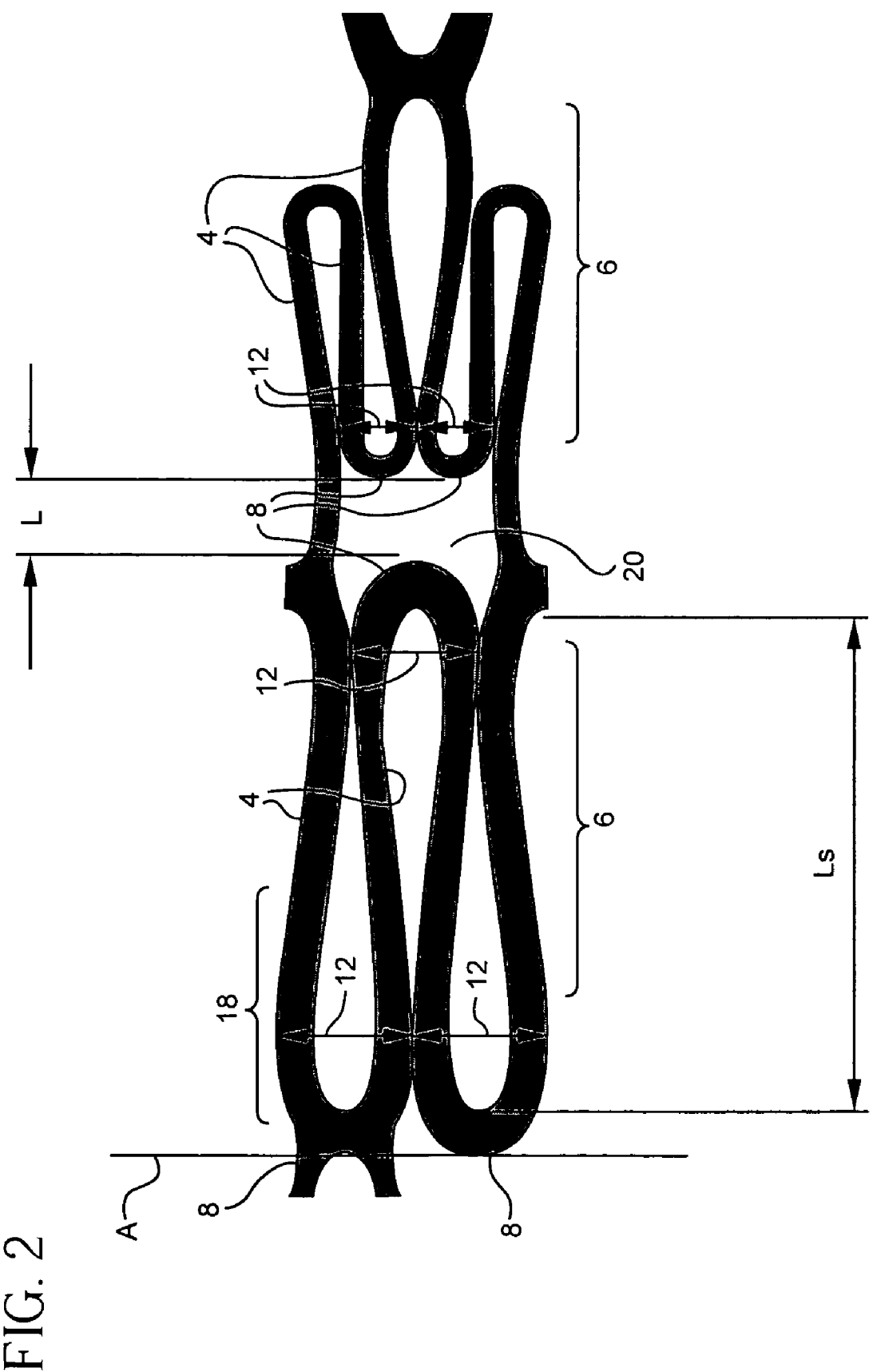
FIG. 2 is an enlarged partial top view of FIG. 1.

FIG. 2 illustrates a fully compressed cell 20 of a conventional stent. As shown in FIG. 2, cell 20 comprises two serpentine sections 6 extending in the circumferential direction. Cell 20 has a longitudinal length "L" between the apexes of interior loops 8 of serpentine sections 6. As further shown in FIG. 2, the apexes of adjacent loops 8 on the left-hand side of the cell are aligned along an axis "A". Struts 4 on the left-hand side of the cell have a uniform strut length denoted as "LS". It will be appreciated that because the left-hand side serpentine section 6 of cell 20 has uniform strut lengths "LS" and loop apexes commonly aligned along axis "A" the largest circumferential widths 12 of adjacent sets of loop 8 and adjoining struts 4 are aligned and form contact site 16 which prevents further circumferential compression of cell 20.

Figure 3:
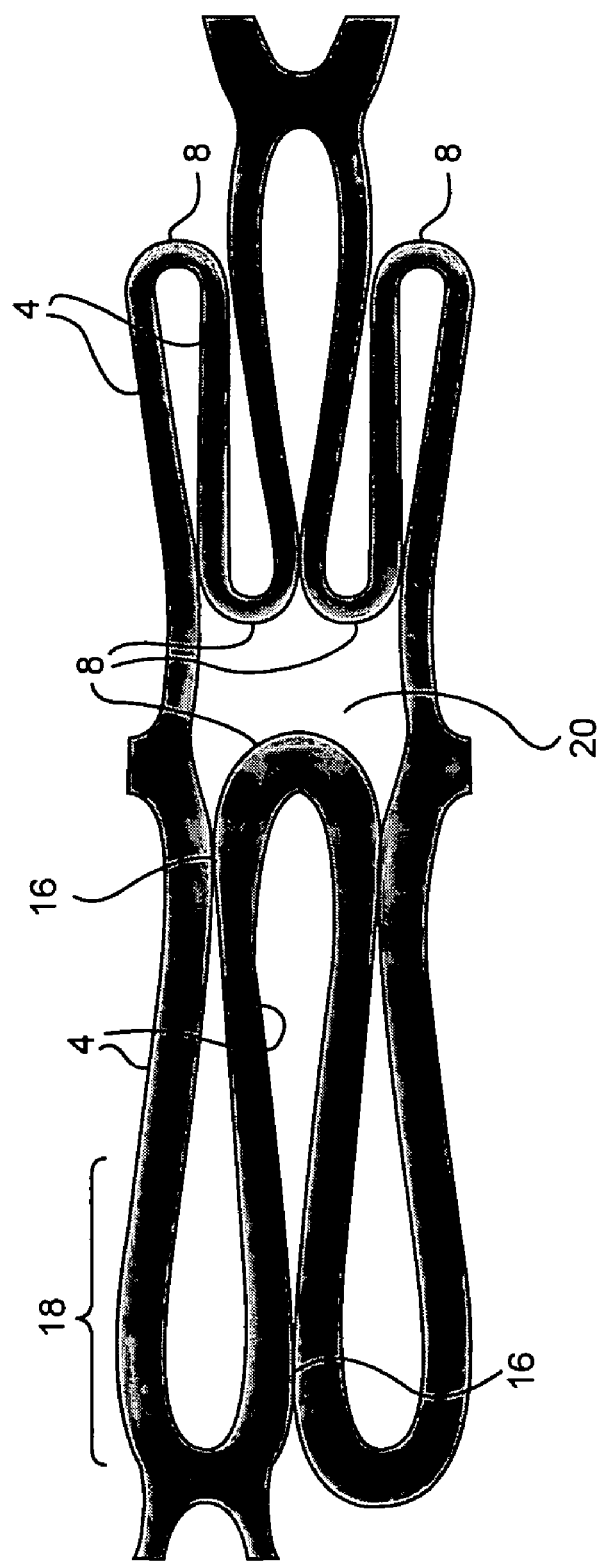
FIG. 3 is a computer-generated analysis of the structure in FIG. 2 illustrating the stress/strain distribution of the compressed stent.

FIG. 3 illustrates a computer-generated analysis of associated stress/strain imparted on a conventional stent when it is compressed. The color of the stent denotes the amount of stress/strain imparted on various portions of the stent. High levels of stress/strain are colored in red. Low levels are colored in blue. The remainder of the color code in decreasing levels of stress/strain includes the colors orange, yellow, light green, green, light blue and blue. As shown in FIG. 3, the highest levels of stress/strain are concentrated in the outside portions of loops 8 and contact sites 16 between adjacent struts 4. The portions of the stent subjected to the highest levels of stress/strain may permanently deform if the stress/strain levels exceed the elastic limits of the stent material. If any portion of the stent becomes permanently deformed, the stent may not fully expand when deployed. It will be understood that the loop portions of the stent are more susceptible to deformation than the strut portions when subjected to high levels of stress/strain. In contrast, the strut portions of the stent can better accommodate high concentrations of stress/strain. This is because the portions of the stent that can withstand higher levels of stress/strain are in the direction of material rolling. It will be understood that the direction of material rolling means the direction of the stent that exhibits the highest strength, either due to material orientation or manufacturing direction of the stent, for example as in the rolling or calendaring of a flat sheet of metal.

Figure 4:
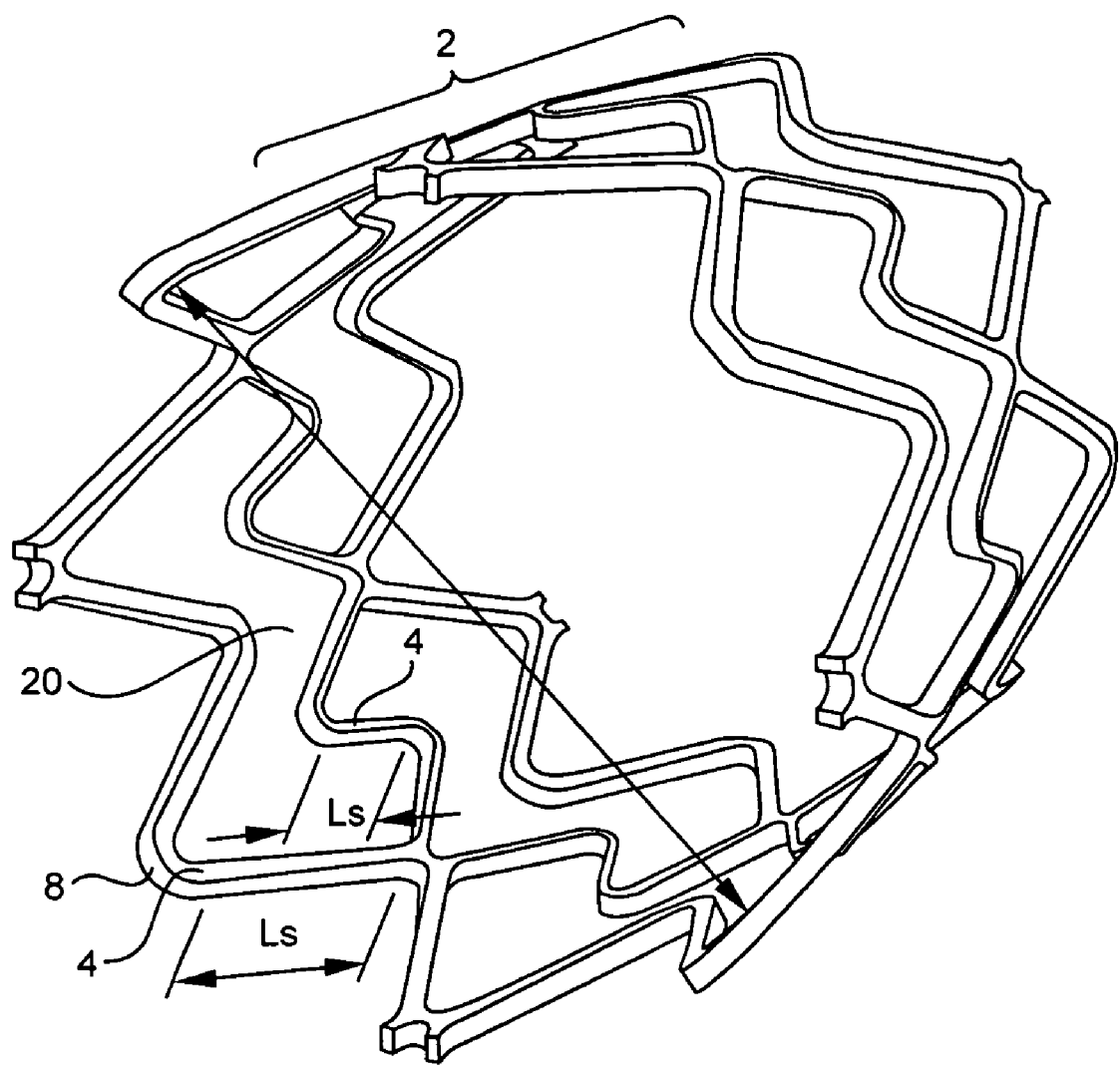
FIG. 4 is a perspective view of the stent in FIG. 1 in the expanded state.
Figure 5:
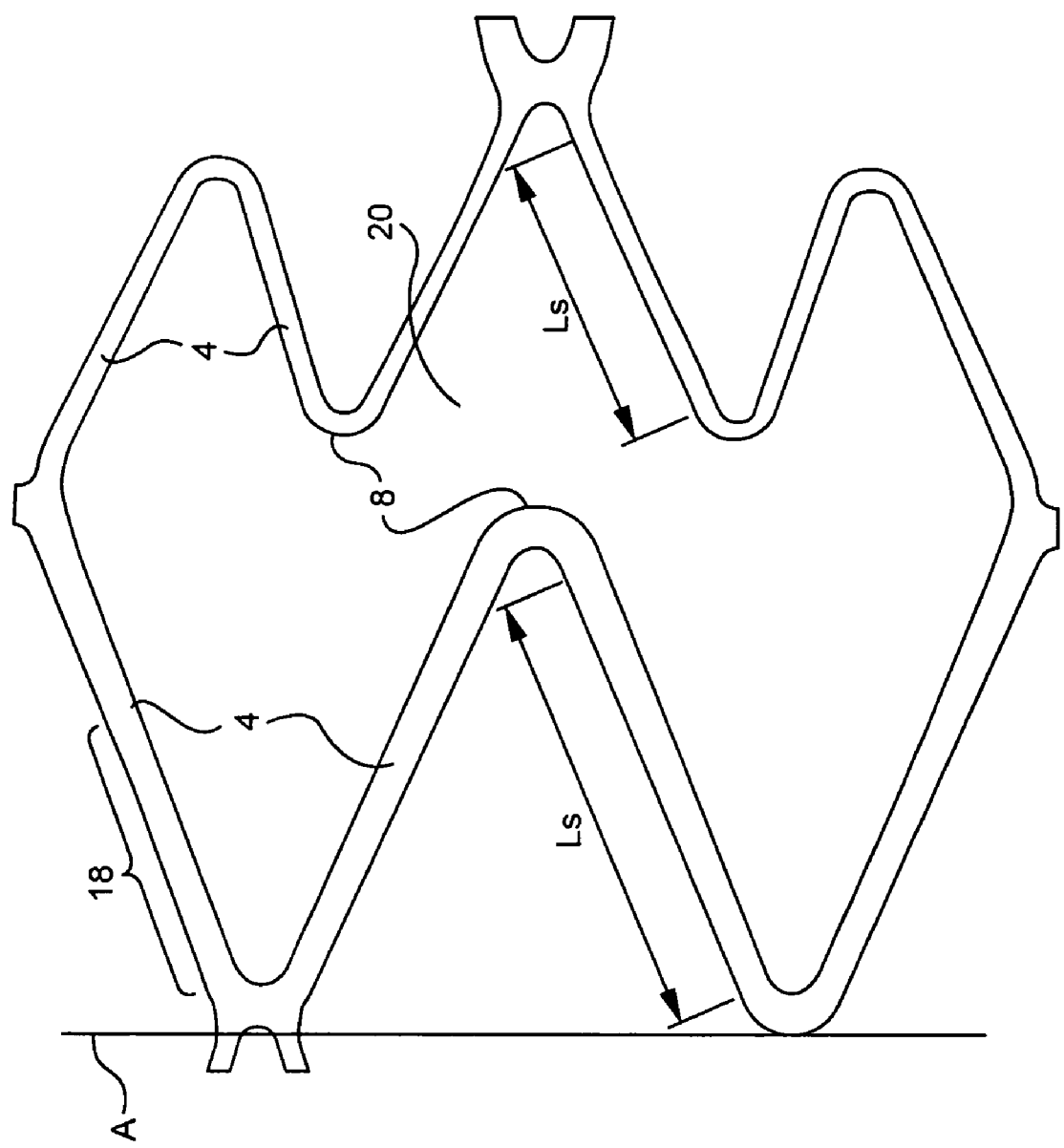
FIG. 5 is an enlarged partial top view of FIG. 4.

In the expanded state, the conventional stent as illustrated in FIG. 4 has an outside diameter 22. The length "LS" of the struts 4 determines the extent to which the stent will expand. FIG. 5 illustrates a cell 20 of the expanded conventional stent to further demonstrate that the stent's expanded diameter is restricted by the struts length "LS". It will be understood that the longer the strut length "LS," the longer the distance between adjacent loops 8 as measured along axis A when the stent is expanded. Thus, a stent having cells 20 with longer strut length "LS" will have greater radial expansion than a stent having cells with shorter strut length "LS."

Figure 6:
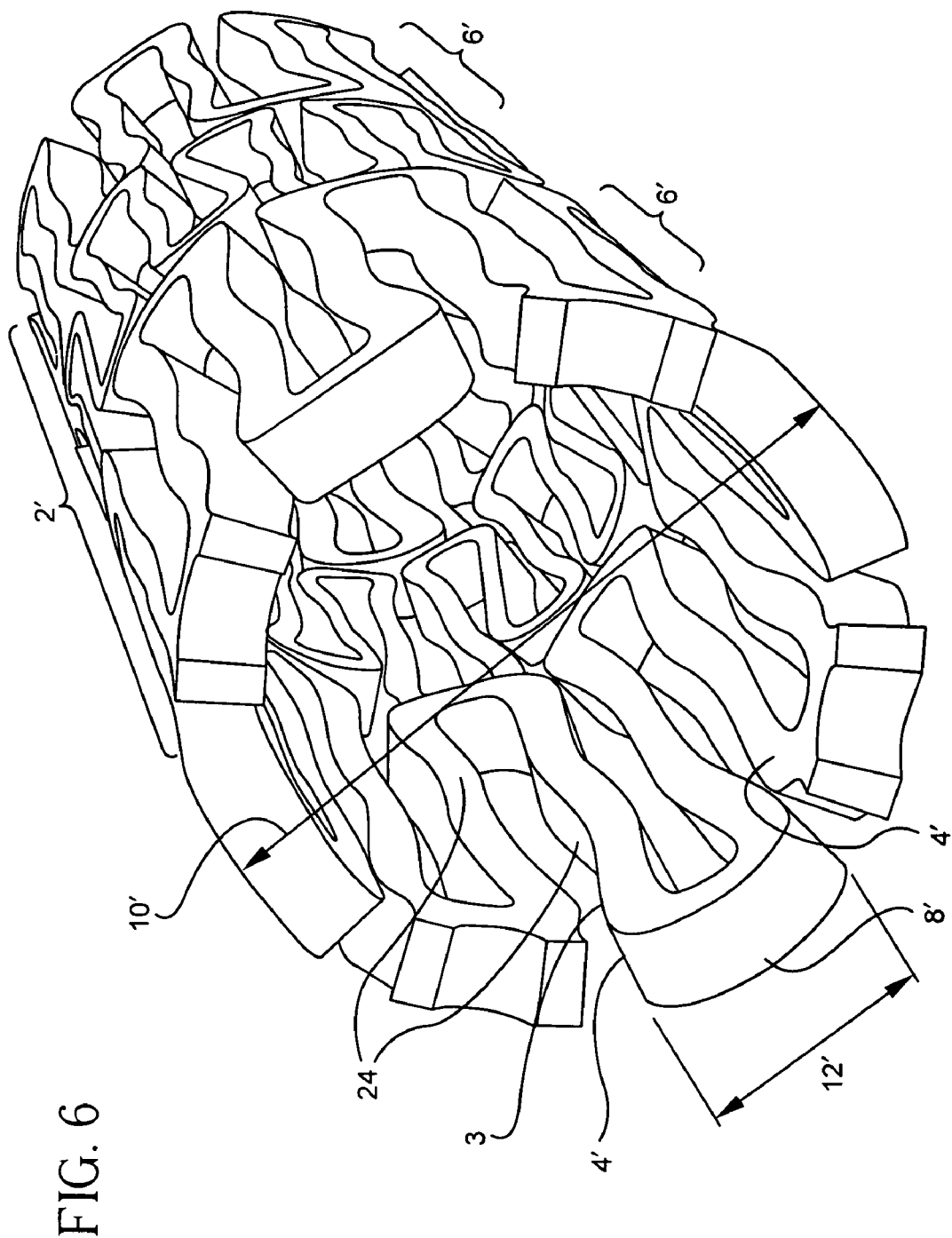
FIG. 6 is a perspective view of a stent portion of one embodiment of the present invention in the compressed state.

FIG. 6 illustrates a stent utilizing features of the present invention. The present invention is not limited to the structure of the stent shown in FIG. 6, and can be used with any stent structure that contains a serpentine section of any size or number of loops and struts.

As shown in FIG. 6, stent 2' is in the compressed state. Due to the modified strut structure 4', the circumferential width 12' of each loop 8' and adjoining struts 4' is reduced relative to that of the conventional stent shown in FIGS. 1-3. Accordingly, the outside diameter 10' of stent 2' is also reduced relative to that of the conventional stent of FIGS. 1-3.

Figure 7:
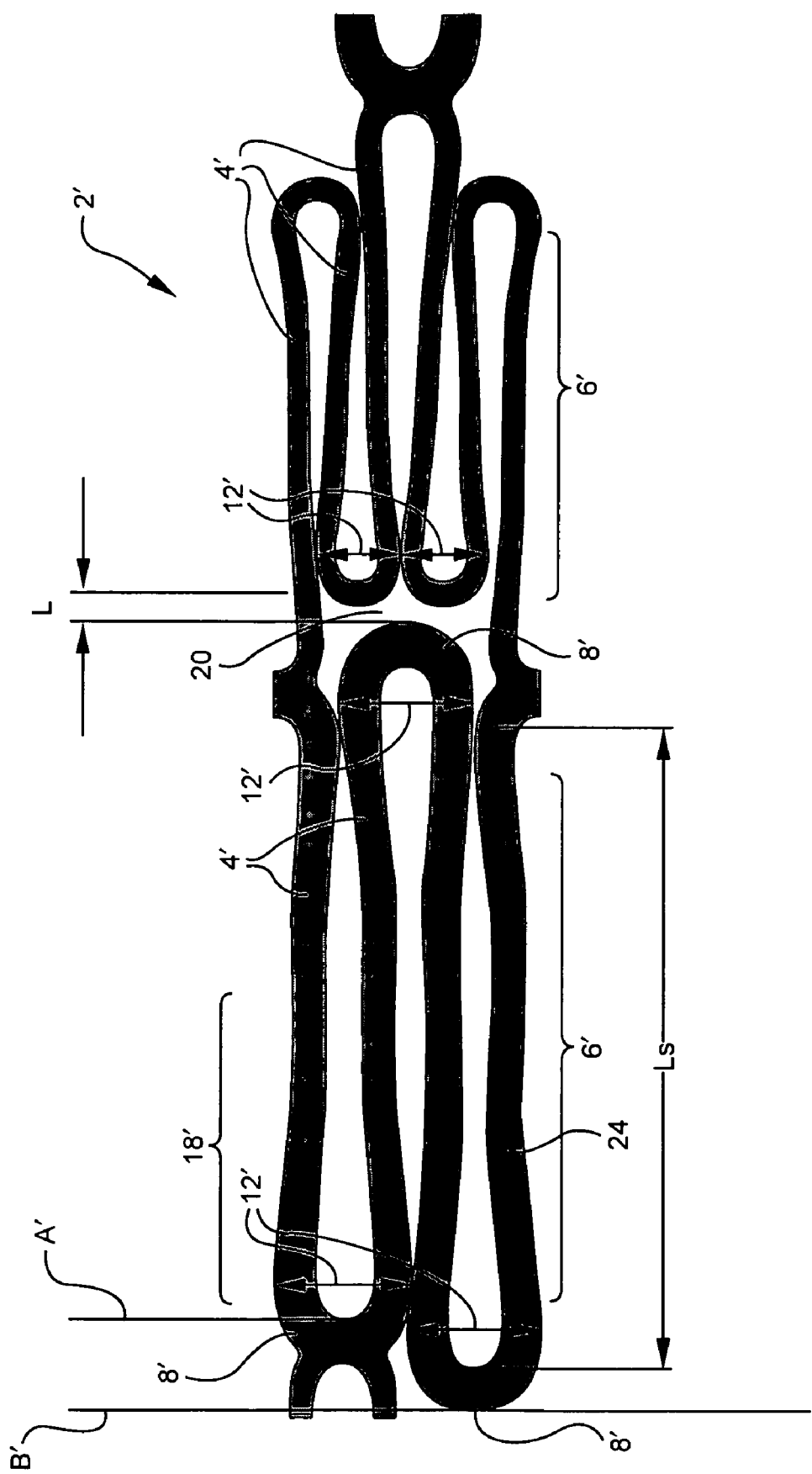
FIG. 7 is an enlarged partial top view of FIG. 6.

FIG. 7 illustrates a cell 20' of a stent of the present invention in a compressed state. The curved strut when the stent is compressed will straighten and the largest circumferential width 12' formed by of each set of loop 8' and adjoining struts 4' will be significantly reduced compared to a conventional stent having bowed regions 18 as shown in FIGS. 1-3. Therefore, the outside diameter of the stent 2' in the compressed state is significantly less than the outside diameter of the conventional stent 2 in the compressed state. In prototype testing, comparing the stent design of the conventional stent 2 and the modification in stent 2', the outside diameter of the stent 2' in the compressed state decreased from 1.9 mm for the conventional stent to 1.3 mm for the modified stent with all other testing parameters being equal. The conventional stent has an expanded to compressed outside diameter ratio of up to about 5:1. The various embodiments of the stent of the present invention can provide an expansion to compression ratio of about 7:1. Again, this modification can be used in any stent design. The invention is not limited to these exemplary stent structures. Further optimization is achieved in stent 2' as described below.

A comparison of FIG. 2 and FIG. 7 illustrates how optimization of the strut length "LS" can be achieved to increase the expanded stent diameter of the stent 2' without increasing either the stress/strain or the compressed diameter of the stent. As illustrated in FIG. 2, the adjacent struts 4 have the same strut length LS. Accordingly, the largest circumferential width 12 of adjacent loops 8 is aligned with each other and interferes with each other when the stent is fully compressed. This configuration in a conventional stent limits the possibility of further reducing the compressed stent's outside diameter.

As shown in FIG. 7, the adjacent struts 4' having varying lengths "LS'" such that the largest circumferential width 12' of one set of loop 8' and adjoining struts 4' will be offset from the largest circumferential width 12' of the adjacent sets of loop 8' and struts 4'. This is further shown by the axially offset positions of the apexes of adjacent loops 8' of stent 2'. As shown in FIG. 7, the apexes of adjacent loops 8' now fall along axis "A'" and axis "B," respectively. This modification provides a decreased outside diameter of the stent in the compressed state because the largest circumferential widths of adjacent sets of loop 8' and adjoining struts 4' no longer interfere with each other and an increased expanded diameter because some of the struts 4' have been lengthened.

As further illustrated in FIG. 7, the increased and varied strut lengths "LS" can also result in an optimization of the area within cell 20'. The lengths "LS" of the struts adjoining the interior loop of serpentine section 6' forming the left-hand side of cell 20' can be increased to laterally offset the interior loop 8' within cell 20'. As shown in FIG. 7, interior loop 12' is axially offset within cell 20' such that the largest circumferential width 12' of the interior set of loop 8' and adjoining struts 4' is not laterally aligned with the largest circumferential width of adjacent sets of loop 8' and adjoining struts 4'. Accordingly, the cell 20' of the embodiment of the present invention shown in FIG. 7 will have a much shorter length "L" than that of the conventional stent as shown in FIG. 2. This, in turn, further allows the compressed stent of the present invention to have a reduced outside diameter compared to the compressed conventional stent illustrated in FIG. 1.

Figure 8:
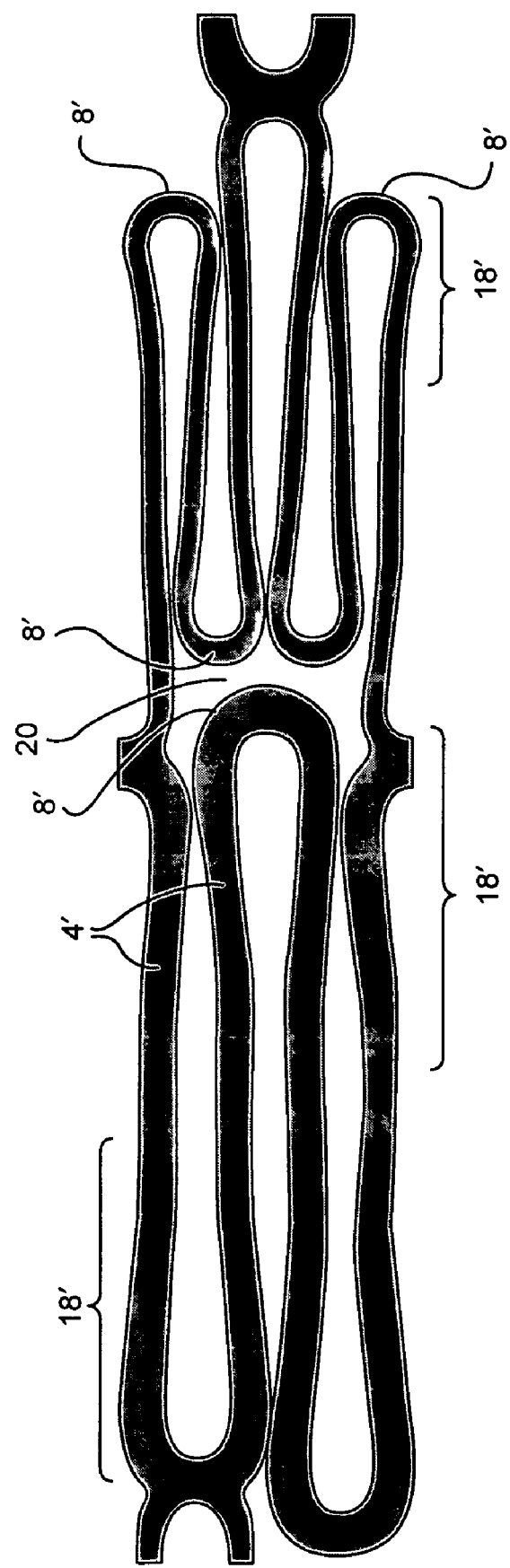
FIG. 8 a computer-generated analysis of the structure in FIG. 7 illustrating the stress/strain distribution of the compressed stent.

FIG. 8 illustrates a computer generated analysis of the stress/strain imparted on a portion of stent 2' when it is compressed. Referring back to FIG. 3, it can be seen that the high stress/strain levels of the conventional stent are concentrated in the loop portions 8 of the stent. Since the loop portions of the stent have the lowest elastic limits, this can lead to permanent deformation of the stent. As shown in FIG. 8, the stress/strain levels imparted on the stent of the present invention were significantly reduced. In addition, the highest concentrations of stress/strain were redistributed from the loops 8' to the adjoining struts 4', which can accommodate higher stress/strain loads without deforming.

Various features of the stent of the present invention may contribute to the redistribution of stress/strain loads from the loop portions to the strut portions of the stent. First, the reverse direction curvature design of the struts 4' provide the struts 4' with increased flexibility compared to the loop portions 8 of stent 2'. According to this design, the greatest flexibility of strut 4' is at the junction in the mid-section of the stent where opposing curved portions 24' join together. Therefore, when stent 2' is compressed the highest levels of stress/strain will be redistributed from the loop portions toward the strut portions.

Figure 11:
FIG. 11 is an enlarged top view of a computer-generated analysis of a strut section from a conventional stent illustrating the stress/strain distribution when the stent is exposed to an external force.
Figure 12:
FIG. 12 is an enlarged top view of a computer-generated analysis of a strut section illustrating the stress/strain distribution of a stent having narrowing struts without reverse curvature when the stent is exposed to an external force.
Figure 13:
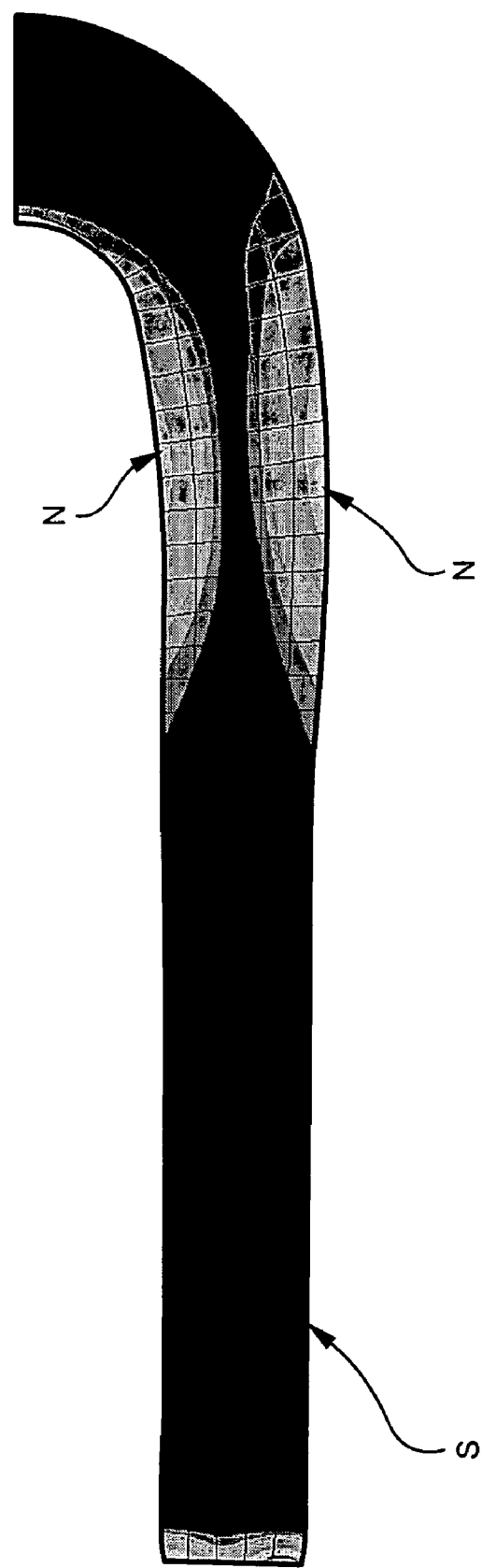
FIG. 13 is a computer-generated analysis of a strut section from the structure in FIG. 12 illustrating optimal stress/strain distribution of a stent having narrowing struts with reverse curvature when the stent is exposed to an external force.

In addition, the properties of the material forming the loop 8' and connecting struts 4' can be varied to redistribute the stress/strain to the strut portions of the stent. As shown in FIG. 11, in a conventional stent having a cell structure with loop and strut portions of uniform dimensions, the high levels of stress/strain will be concentrated in the loop portions at areas M. If radial forces exceeding the elastic limit of the stent are applied to stent when compressing the stent to the catheter balloon, the stent will be permanently deformed and will not fully expand when deployed. Referring now to FIG. 12, it can be seen that by increasing the cross-sectional area in the loop section 8' and gradually reducing the cross-sectional area of struts 4', the highest levels of stress/strain imparted on the stent can be reduced and redistributed from the loop portion to the strut portions of the stent.

Figure 9:
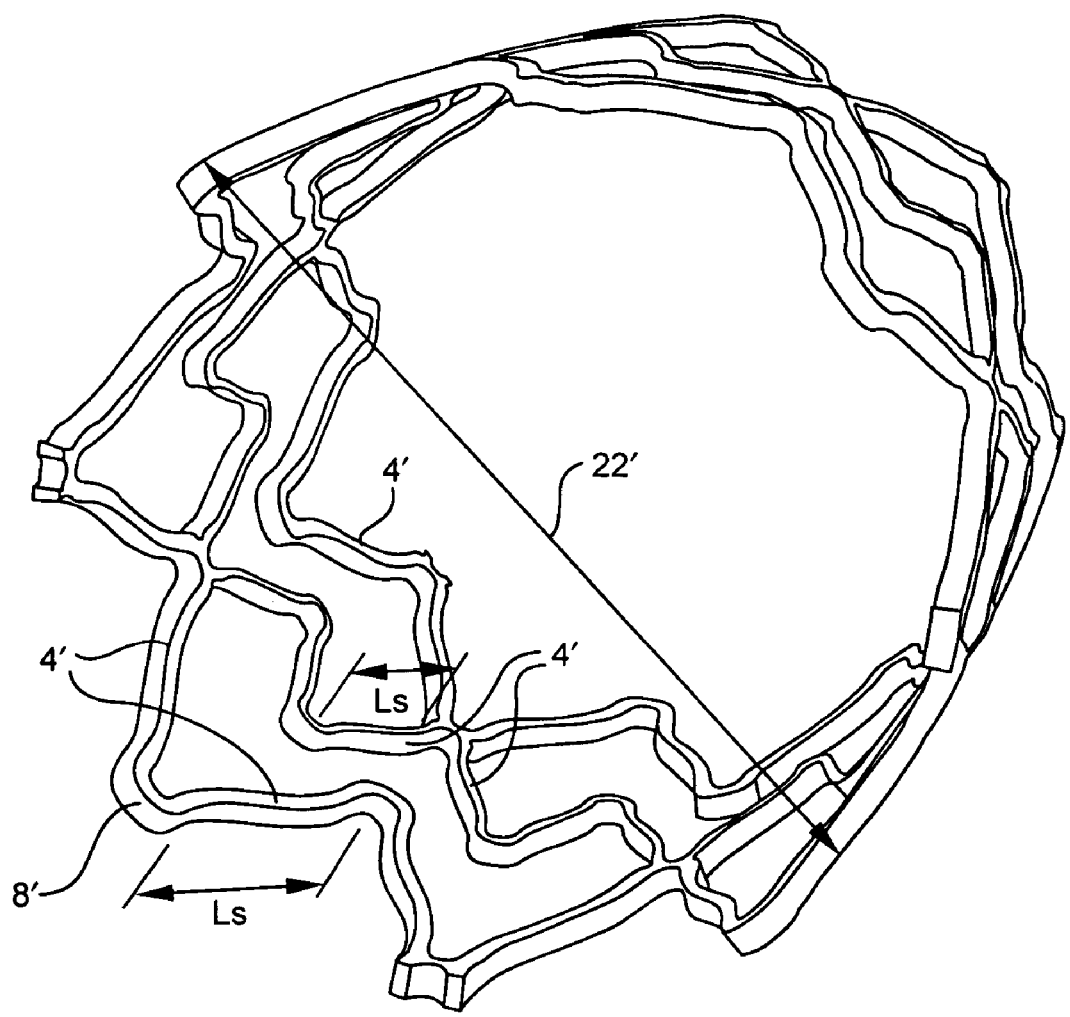
FIG. 9 is a perspective view of the stent in FIG. 6 in the expanded state.

FIG. 9 illustrates stent 2' with the reverse direction curvature strut design in the expanded state. Outside diameter 22' is maximized by increasing strut length "LS", as previously discussed, without compromising the compressed stent diameter or increasing stress/strain. The longer strut length "LS" allows a larger expanded outside diameter of the stent and a smaller compressed diameter than a conventional stent. These comparisons are illustrated in FIGS. 1 and 4 (compressed and expanded states respectively) for the conventional stent, and FIGS. 6 and 9 for the stent with the reverse strut bend.

Figure 10:
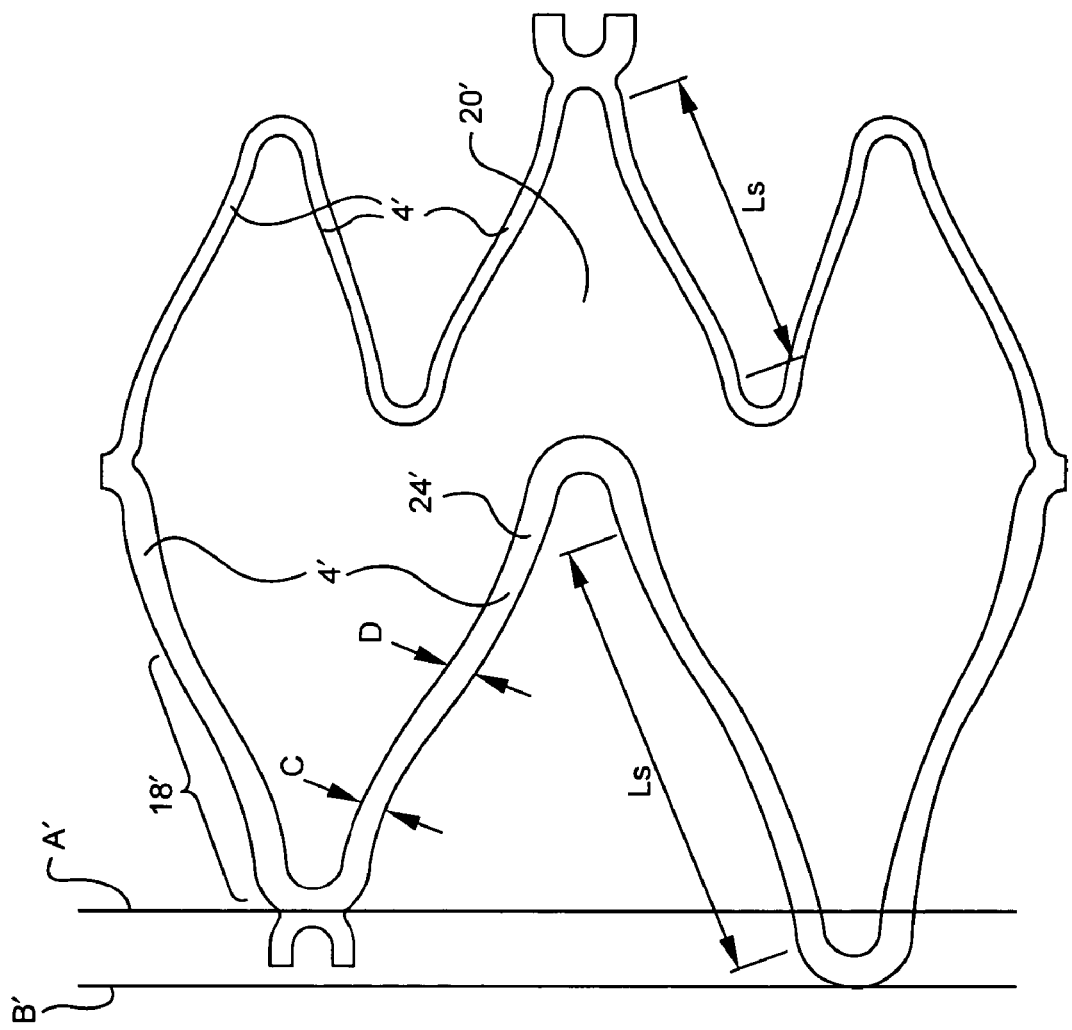
FIG. 10 is an enlarged partial top view of FIG. 9.

FIG. 10 illustrates a portion of stent 2' in the expanded state. Strut 4' contains the reverse strut bend design. Arcuate sections 24 are facing opposite each other and become more curved when expanded as compared to its straighter configuration when strut 4' is compressed. The strut 4' is wider at its ends than its mid-section. See, for example, that strut 4' is wider at location "C" than at location "D". This reduced width assists in transferring the stress/strain distribution. The loops 8' of stent 2' are made wider than attached struts to further transfer maximal strains encountered by the stent to more suitable parts of the stent, namely the strut sections.

It should be understood that the above description is only representative of illustrative examples of embodiments. For the reader's convenience, the above description has focused on a representative sample of all possible embodiments, a sample that teaches the principles of the invention. Other embodiments may result from a different combination of portions of different embodiments. The description has not attempted to exhaustively enumerate all possible variations.

Furthermore, since numerous modifications and variations will readily occur to those skilled in the art, it is not desired that the present invention be limited to the exact construction and operation illustrated. Accordingly, all suitable modifications and equivalents that may be resorted to are intended to fall within the scope of the claims.

What is claimed is:

1. A stent, comprising:
   a plurality of interconnected circumferential bands defining a cylindrical structure having a longitudinal axis;
   each of the circumferential bands having a generally serpentine pattern and comprising a plurality of struts and a plurality of loops, wherein each end of a strut is coupled to an end of a loop;
   at least one of the circumferential bands having at least two consecutive struts comprising a plurality of arcuate sections, wherein each arcuate section in each strut has reverse curvature of opposing arcuate sections extending from each end to the mid-section of the strut wherein the plurality of arcuate sections in the strut substantially straighten during compression of the stent;
   wherein each strut with arcuate sections has a cross-sectional area that is larger at the strut ends than in the midsection of the strut;
   said adjacent struts having varying lengths to produce axially offset positions of adjacent loops.

2. The stent according to claim 1, wherein said stent is self-expanding.

3. The stent according to claim 2, wherein the stent has an expanded to compressed outside diameter ratio of greater than about 5:1.

4. The stent according to claim 2, wherein the stent has an expanded to compressed outside diameter ratio of about 7:1.

5. The stem according to claim 1, wherein said stein is balloon-expandable.

6. The stem according to claim 1, wherein the width of the loop is greater than the width of the strut.

7. The stem according to claim 1, wherein maximal strain imparted on the stent when the stem is compressed is distributed toward the mid-section of the struts.

8. The stem according to claim 1, wherein said at least one circumferential band includes at least one set of two struts with arcuate sections coupled to the ends of one loop, said set of loop and struts having a maximum circumferential width when the stem is compressed, the maximum circumferential width of each set of loop and struts being offset along the longitudinal axis from maximum circumferential widths of adjacent sets of loop and struts when the stem is compressed.

9. A stent, comprising:
   a plurality of interconnected circumferential bands defining a cylindrical structure having a longitudinal axis;
   each of the circumferential bands having a generally serpentine pattern and comprising a plurality of struts and a plurality of loops, wherein each end of a loop is coupled to an end of two adjacent struts;
   at least one circumferential band having consecutive struts comprising a plurality of arcuate sections, wherein each arcuate section in each strut has reverse curvature of opposing arcuate sections extending from each end to the mid-section of the strut and each strut has a varying width wherein the width at ends of the strut are larger than the width of the remainder of the strut;
   wherein the plurality of arcuate sections in the strut substantially straighten during compression of the stent;
   wherein each strut with arcuate sections has a cross-sectional area that gradually decreases in opposing directions from the ends of the strut, the ends of the strut having greater cross-sectional area than the mid-section of the strut;
   said adjacent struts having varying lengths which result in axially offset adjacent loops.

10. The stent according to claim 9, wherein said stent is self-expanding.

11. The stem according to claim 10, wherein the stent has an expanded to compressed outside diameter ratio of greater than about 5:1.

12. The stent according to claim 10, wherein the stent has an expanded to compressed outer diameter ratio of about 7:1.

13. The stem according to claim 9, wherein said stent is balloon-expandable.

14. The stem according to claim 9, wherein said loop is wider than said strut.

15. The stent according to claim 9, wherein said at least one circumferential band comprises a multiplicity of sets of two adjacent struts coupled to the ends of a loop, each set of loop and struts having a maximum circumferential width when the stent is compressed, the maximum circumferential widths of adjacent sets of loop and struts being offset along the longitudinal axis when the stent is compressed.

16. A stein defining a cylindrical structure having a longitudinal axis comprising a plurality of cells, each of the plurality of cells comprising:
   a first circumferential section having a generally serpentine pattern and comprising a plurality of struts and at least one loop, the struts and loops forming at least one set of two struts coupled to the ends of one loop;
   a second circumferential section having a generally serpentine pattern and comprising a plurality of struts and at least one loop;
   at least one of the sets of the first circumferential section having two consecutive struts comprising a plurality of arcuate sections, wherein each arcuate section has reverse curvature of opposing arcuate sections extending from each end to the mid-section of the strut, and each strut has a varying width wherein the width at ends of each strut are larger than the width of the remainder of the same strut and the loop has a greater width than each strut;
   wherein the plurality of arcuate sections in the strict substantially straighten during compression of the stent;
   wherein each strut with arcuate sections has a cross-sectional area that gradually decreases in opposing directions from the ends of the strut, the ends of the strut having greater cross-sectional area than the mid-section of the strut;

said adjacent struts having varying lengths which result in axially offset adjacent loops.

17. The stent according to claim 16, wherein the stent is self-expanding.

18. The stent according to claim 17, wherein the stent has an expanded to compressed outside diameter ratio of greater than about 5:1.

19. The stent according to claim 17, wherein the stent has an expanded to compressed outside diameter ratio of about 7:1.

20. The stent according to claim 16, wherein said stent is balloon-expandable.

21. The stent according to claim 16, wherein said loop is wider than said strut.

22. The stent according to claim 16, wherein each set of loop and struts in the first circumferential section has a maximum circumferential width when the stent is compressed, the maximum circumferential width of each set of loop and struts being offset along the longitudinal axis from maximum circumferential widths of adjacent sets of loop and struts when the stem is compressed.

* * * * *